United States Patent [19]

Picken, Jr.

[11] Patent Number: 5,853,730
[45] Date of Patent: Dec. 29, 1998

[54] CLEANING SOLUTION USING CITRUS WATER DISTILLATE

[76] Inventor: Henry M. Picken, Jr., 1500 Beaumont Dr., Kennesaw, Ga. 30144

[21] Appl. No.: 829,228

[22] Filed: Mar. 31, 1997

Related U.S. Application Data

[63] Continuation-in-part of Ser. No. 702,769, Aug. 22, 1996, Pat. No. 5,741,481.

[51] Int. Cl.$^6$ ..................................................... C11D 7/44
[52] U.S. Cl. ........................ 424/195.1; 510/109; 510/110; 510/111; 510/364; 510/365
[58] Field of Search ................................. 424/74, 195.1; 510/109, 110, 111, 364, 365

[56] References Cited

U.S. PATENT DOCUMENTS

| | | | |
|---|---|---|---|
| Re. 29,649 | 5/1978 | Farnsworth | 252/171 |
| 3,862,014 | 1/1975 | Atkins et al. | 202/204 |
| 3,899,398 | 8/1975 | Cole et al. | 201/2.5 |
| 3,933,674 | 1/1976 | Farnsworth | 252/171 |
| 4,297,374 | 10/1981 | Wess | 514/777 |
| 4,374,865 | 2/1983 | Strobel | 426/599 |
| 4,608,266 | 8/1986 | Epperson et al. | 426/599 |
| 4,811,747 | 3/1989 | Reis | 132/203 |
| 4,849,214 | 7/1989 | Ruiseco | 424/74 |
| 4,855,137 | 8/1989 | Keri et al. | 424/195.1 |
| 5,063,062 | 11/1991 | Greenspan et al. | 424/443 |
| 5,167,954 | 12/1992 | Frey | 424/74 |
| 5,534,274 | 7/1996 | DeStefano | 426/66 |
| 5,741,481 | 4/1998 | Picken, Jr. | 424/74 |

FOREIGN PATENT DOCUMENTS

| | | |
|---|---|---|
| 2131067 | 1/1973 | Germany . |
| 63-084457 | 4/1988 | Japan . |
| 01-254629 | 10/1989 | Japan . |
| 2010892 | 7/1979 | United Kingdom . |

OTHER PUBLICATIONS

Coleman et al., "Potential Uses of Distilled Orange Oils", The Citrus Industry, Published in Mar. 1974, vol. 55, No. 2, pp. 20–21.

*Primary Examiner*—Robert H. Harrison
*Attorney, Agent, or Firm*—Thomas, Kayden, Horstemeyer & Risley, LLP

[57] ABSTRACT

A citrus scented cosmetic is described wherein citrus water distillate is substituted for some or all of the distilled and/or deionized water typically used as an ingredient in the cosmetic. Citrus water distillate is an economical, environmentally-friendly source of purified "soft" water which imparts a natural citrus odor to the cosmetic.

4 Claims, No Drawings

CLEANING SOLUTION USING CITRUS WATER DISTILLATE

This application is a continuation-in-part of application Ser. No. 08/702,769, filed Aug. 22, 1996, now U.S. Pat. No. 5,741,481 titled COSMETICS CONTAINING CITRUS WATER DISTILLATE.

FIELD OF INVENTION

The present invention relates generally to the manufacture of hair care products and other cosmetics. More specifically, the invention relates to the use of the distillate obtained from the concentration of citrus juice as a liquid component of cosmetic products.

BACKGROUND OF THE INVENTION

Cosmetics require ultra-pure starting materials and typically the liquid component of cosmetic products is deionized or distilled water. The production of distilled water involves essentially the evaporation and later collection of pure water away from the impurities contained within the impure water. Deionization is the removal of charged particles from water by bringing it in contact with some reacting, deionizing material. These processes require time expenditure and energy consumption and thus add to the cost of cosmetic preparation. Various hair cosmetics, i.e. shampoos, conditioners, hair sprays require different manufacturing formulas to accomplish different objectives (cleansing, conditioning, fixation) but all have water as a major ingredient. Thus, it is important to ensure a source of pure water for production.

Citrus water distillate is produced during the process of concentrating citrus fruit juice, such as orange juice, lemon juice, grapefruit juice, to produce juice concentrate. Citrus fruit juice is typically concentrated so that the storage, shipping and preparation of fresh and frozen citrus products is more manageable. Typically in the industry the citrus water distillate is thrown away or is used to irrigate the citrus trees. This distillate, however, is extremely purified, having been filtered both naturally, by the citrus trees, and during the process of juice concentration. The distillate contains very low amounts of ionic and mineral components, thus it comprises "soft" water. Soft water is preferable for cosmetic preparation because it provides a better. lather and does not leave a residue when rinsed off.

A recent disclosure of the use of citrus water distillate is found in the publication *Beverage Industry,* "Annual Soft Drink Report", page 18. The author discloses the use of citrus water distillate as bottled water for consumption. The author does not, however, teach the use of distillate in cosmetics. Other prior art teaches the use of orange flower water and water derived from orange peels in the preparation of cosmetics. For example, U.S. Pat. No. 5,167,954 to Frey teaches the use of orange flower water in the preparation of hair lotion. U.S. Pat. No. 5,063,062 to Greenspan et al. teaches the inclusion of orange oil, oil from the peel of oranges, in a cleaning composition for human skin. U.S. Pat. No. 4,849,214 to Ruiseco teaches the use of orange water in a hair treatment. The orange water taught therein is prepared by crushing orange peel and/or pulp and rinsing the crushed orange parts with water. U.S. Pat. No. 4,811,747 to Reis teaches the use of orange juice as a hair treatment. None of the prior art references teach using the distillate from the process of concentrating citrus juice as an ingredient in cosmetics.

SUMMARY OF THE INVENTION

An object of the present invention is to overcome the deficiencies and inadequacies of the prior art as described above and as generally known in the industry by providing citrus water distillate as a liquid component of cosmetics, specifically, hair care products.

Another object of the present invention is to provide a source of natural citrus odor for cosmetic products.

A further object of the present invention is to ensure a source of "soft" water for use in the production of cosmetics.

A still further object of the present invention is to eliminate the need to distill water for the production of cosmetics and to reduce the production costs of cosmetic products and conserve energy required in the production of cosmetic products.

An additional object of the present invention is to provide an economically beneficial use for the distillate produced from the concentration of citrus juice.

Briefly described, the present invention is a novel use for citrus water distillate, a byproduct of the citrus juice industry which has heretofore not been economically utilized. The present invention is the use of this distillate in cosmetics, particularly hair care products. Essentially, the distillate is substituted for the distilled water ordinarily used in preparation of the cosmetic.

An example of a cosmetic which is prepared by the present invention is shampoo. The citrus water distillate is combined with a detergent, surfactants, a preservative, coloring agent and a thickening agent to yield a citrus-scented hair shampoo which provides good lather and imparts a shiny and clean appearance to hair.

The method of preparation of cosmetics as taught by the present invention is advantageous because the processing costs for the cosmetic are reduced because there are no energy costs entailed in producing distilled water.

Another advantage of the present invention is that it ensures an excellent source of "soft" water for cosmetic production, water which does not contain ionic compounds or minerals and so provides a better lather and does not leave a "hard" water residue (soap scum).

Another advantage of the present invention is that the distillate is a source of natural citrus odor and oils for the cosmetic.

In furtherance of the above objects, the following detailed description provides direction in implementing the invention. Other objects, features and advantages of the invention will hereinafter become more readily apparent from the following description.

DETAILED DESCRIPTION OF THE PREFERRED EMBODIMENTS

Citrus water distillate is collected as a byproduct of the concentration of citrus juice into citrus juice concentrate. This distillate is extremely pure, containing essentially purified $H_2O$ and a small amount of d-limonene which is a component found in the rinds of citrus fruit. The citrus water distillate is substituted, in approximately an equivalent amount, for water in preparation of cosmetic products. As an example, a shampoo was prepared containing 35 –90% Citrus Water Distillate, Sodium Laureth Sulfate, Sodium Cocamphodipropionate, Tea-Lauryl Sulfate, Cocamidopropyl Betaine, Cocamide Dea, Orange Essential Oils, Propylene Glycol, Diazolidinyl Urea, Methylparaben, Propylparaben, Citric Acid, Sodium Chloride, Polyquaternium-10, FD&C Yellow #5, and D&C Red 33. Citric acid or a similar compound was used to adjust the pH of the shampoo to a pH substantially equivalent to or compatible with human skin.

This formula produced a viscous liquid with orange color and citrus fragrance. It provided good lather and left hair shiny and manageable.

A non-aerosol hairspray was prepared with 50–90% SD Alcohol 40, 5–20% Citrus Water Distillate, VA Crotonates/Vinyl Neodecanoate Copolymer, Octylacrylamide/Acrylates/Butylaminoethyl Methacrylate Copolymer, AMP, Citrus Essential Oils, Dimethicone Copolyol and Cocamidopropyl Betaine.

A hair conditioner was prepared with the following ingredients: 50–95% Citrus Water Distillate, Stearyldimethylbenzyl Ammonium Chloride, Cetearyl Alcohol Ceteareth-20, Glycerin, Guar Hydroxypropyltrimonium Chloride, Grapefruit Essential Oils, Amodimethicone, Tallow Trimonium Chloride, Nonoxnol-10, Polyquaternium-10, Hydrolyzed Collagen, Citric Acid, Quaternium-80, FD&C Yellow #5, Myristalkonium Chloride, and Quaternium-14.

The conditioner prepared according to this formula left hair manageable, soft and shiny. The hair also was left with a pleasant citrus scent.

In formulating cosmetics various components are selected according to the intended use of the product and may include detergents, surfactants, thickening agents, preservatives, coloring agents, fragrances, acids or bases to adjust the pH, and water. It is the latter component that, in most cases, is the principal ingredient, and to which the present invention is primarily directed. The amount of the citrus water distillate can vary between approximately five to ninety percent by weight of the cosmetic formulation. The distillate is typically free of minerals, i.e. "soft" water, and free of contaminants due to the natural filtration which occurs as the trees or plants produce the citrus fruit.

An alternate embodiment of a product utilizing the distillate from the process of concentrating citrus juice is a washing or rinsing agent for agricultural products, i.e., fruits, vegetables and the like and a method of producing same. While the discussion below focuses on fruits and vegetables, other products, such as fibrous plants used to produce textiles, may be treated using the present invention. In addition, the cleaning solution of the present invention may be used for other cleaning functions. Thus, as will be appreciated by those of ordinary skill in the art, the discussion is not to be taken as limiting in any respect.

Agricultural products are commonly treated with pesticides, fungicides, selected herbicides, waxes and other chemicals either before, during, or after growth. Such chemicals typically contain a hydrocarbon component such as a petroleum or a derivative thereof, in order to impart water resistance to the chemical. This is necessary to prevent the chemical from being washed off the plant or product by rain. This property virtually ensures that the products will reach the market with a chemical residue that is difficult or impossible to remove utilizing water alone.

This embodiment of the invention contains some or all of the following components: citrus water distillate, sodium citrate, and a surfactant such as potassium linoleate ethyl alcohol, sodium laural sulfate or the like. The citrus water distillate may comprise as much as ninety-five percent (95%) of the solution. This distillate contains some of the natural citrus oils and other components which are natural solvents. The solvent component or components break down the chemical bonds of the pesticide, etc., which impart the water resistancy to the chemical.

Sodium citrate is a natural salt of citric acid and a derivative of citrus fruit. This component is used as a natural "builder" which softens water and improves its cleaning ability. The surfactant component is preferably a natural product. Potassium linoleate ethyl alcohol is a sugar-starch based surfactant. Sodium laural sulfate is a surfactant derived from coconut oil. The surfactant binds with the dissociated chemical pesticide, fungicide, etc. so that the residue can be rinsed off the product by the water portion of the present solution.

A formula which has proven effective contains the following components:

| | |
|---|---|
| Citrus water distillate | 95.7% |
| Sodium citrate | 2.2% |
| Potassium linoleate ethyl alcohol | 1.5% |
| Sodium laural sulfate | .6% |

Suitable substitute components and variances in the weight percentages are considered to be within the scope of the present invention. In use, the product to be cleaned is sprayed with or soaked in the present solution and then rinsed with plain water. Contaminant residues are removed leaving a clean, safe product having no aftertaste.

It will be apparent to those skilled in the art that many modifications may be made to the preferred embodiments of the present invention, as set forth above, without departing substantially from the principles of the present invention. All such modifications are intended to be included herein within the scope of the present invention, as defined in the following claims.

I claim:

1. A solution for removing water resistant, hydrocarbon-based chemical residues from agricultural products comprising:

5–95% by weight citrus water distillate, said distillate produced from the process of concentrating citrus juice; and a surfactant.

2. A solution as defined in claim 1 further comprising sodium citrate.

3. A solution for removing water resistant, hydrocarbon-based residues comprising:

citrus water distillate and a surfactant.

4. A solution for removing water resistant, hydrocarbon-based residues comprising:

citrus water distillate and sodium citrate.

\* \* \* \* \*